United States Patent
Linck

(10) Patent No.: US 7,195,481 B1
(45) Date of Patent: Mar. 27, 2007

(54) ORTHODONTIC DISTRACTOR

(76) Inventor: Donald W. Linck, 3147 Putnam Blvd., Pleasant Hill, CA (US) 94523

( * ) Notice: Subject to any disclaimer, the term of this patent is extended or adjusted under 35 U.S.C. 154(b) by 156 days.

(21) Appl. No.: 10/877,336

(22) Filed: Jun. 28, 2004

Related U.S. Application Data

(60) Provisional application No. 60/540,254, filed on Jan. 30, 2004.

(51) Int. Cl.
*A61C 3/00* (2006.01)
*A61F 5/04* (2006.01)

(52) U.S. Cl. ............................................ 433/7; 606/57

(58) Field of Classification Search .................... 433/7; 606/57–90, 105
See application file for complete search history.

(56) References Cited

U.S. PATENT DOCUMENTS 5,700,263 A * 12/1997 Schendel ...................... 606/57
D460,184 S * 7/2002 Schendel et al. .......... D24/133

* cited by examiner

*Primary Examiner*—Cris Rodriguez
*Assistant Examiner*—Candice C. Stokes
(74) *Attorney, Agent, or Firm*—Rodgers & Rodgers

(57) ABSTRACT

An orthodontic distractor comprising a pair of telescopically interconnected channels, a drive screw operable to withdraw the inner channel from the outer channel and the outer channel being formed in the shape of a logarithmic curve.

4 Claims, 2 Drawing Sheets

ORTHODONTIC DISTRACTOR

The benefits under 35 U.S.C. 119 are claimed of provisional patent application 60/540,254 filed Jan. 30, 2004.

BACKGROUND OF THE INVENTION

In orthopedics in general and, in particular orthodontics, bones are known to develop in terms of size and shape which require that two segments of bone be separated, and held in place relative to each other to allow new bone to grow between the two segments.

Known curved distractors are in the form of a circle segment which limits the distraction distance and is ineffective in correcting larger discrepancies in length.

SUMMARY OF THE INVENTION

According to this invention, an orthodontic distractor is provided and comprises a pair of mounts, a logarithmically curved channel with an extension telescopically disposed therein, the curved channel being secured to one of the mounts, a drive screw being threadedly interconnected to the other mount, and stop means associated with the curved channel to prevent movement of the drive screw within the curved channel.

DETAILED DESCRIPTION OF THE INVENTION

Figure 5:
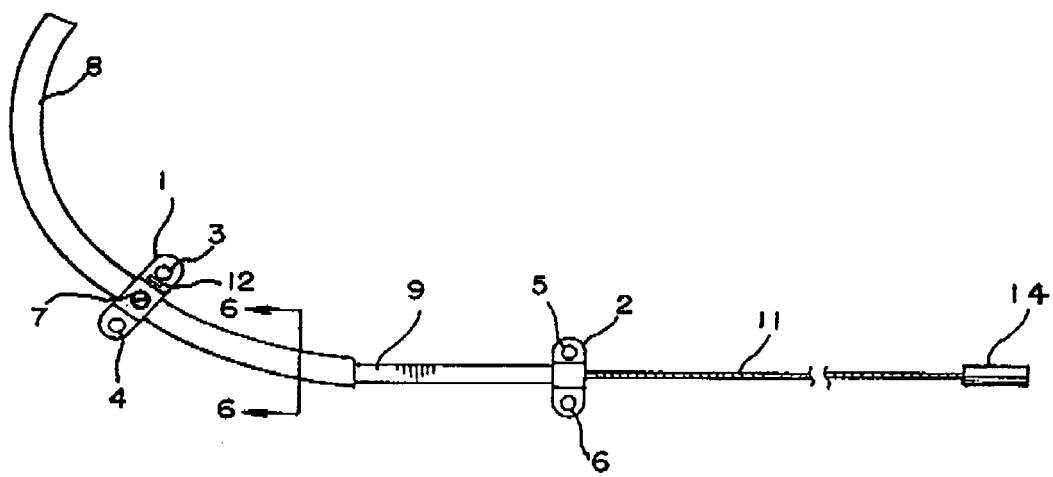
FIG. 5 is a side view of the distractor in the extended position.
Figure 6:
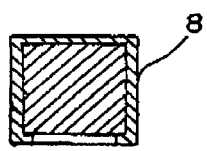
FIG. 6 is a view taken along the line 6—6 in FIG. 5.
Figure 7:
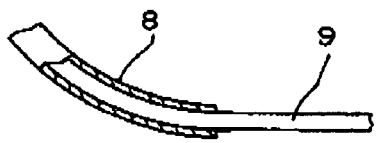
FIG. 7 is an enlarged view showing the telescoping feature of the distractor.

In the drawings and with particular reference to FIG. 5, the basic elements of the distractor are shown wherein the numerals 1 and 2 designate the distractor mounts. Apertures 3 and 4 are formed in mount 1 and apertures 5 and 6 are formed in mount 2. Of course, screws are used in connection with apertures 3–6 for the purpose of attaching the distractor to a patient's bone. In addition, stop means in the form of set screw 7 is disposed in an aperture formed in mount 1.

To complete the basic elements of the distractor according to this invention, curved channel 8, which is in the shape of a logarithmic curve, is provided with hollow telescoping extension 9 disposed therein. For the purpose of allowing escape of any accumulated debris, groove 10 is formed on the inner curved surface of curved channel 8. Also, drive screw 11 cooperates with the internal threads of mount 2 and extends through hollow telescoping extension 9 and into curved channel 8. Stop screw 12 is threaded into mount 1 and insertable into slot 13 or curved channel 8. Finally, nut 14 or the like is formed on the outer end of drive screw 11 such that drive screw 11 is rotated by means of the cooperation of nut 14 and an appropriate manipulation tool such as a wrench.

Figure 1:
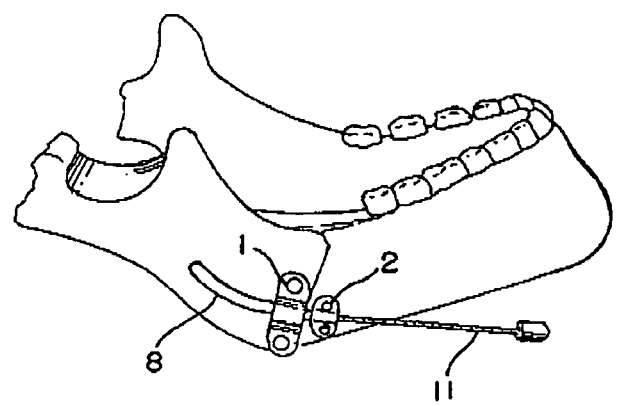
FIG. 1 is a perspective view showing the distractor prior to distraction.

In operation, mount 1 is placed in the desired location in a patient's mouth and secured in place by inserting screws through apertures 3 and 4. Curved channel 8 is moved under mount 1 and into the desired position and then secured in place by tightening set screw 7. Then mount 2 is secured in position by inserting screws through apertures 5 and 6, as is well known. Following this, the distractor appears as essentially shown in FIG. 1.

Figure 2:
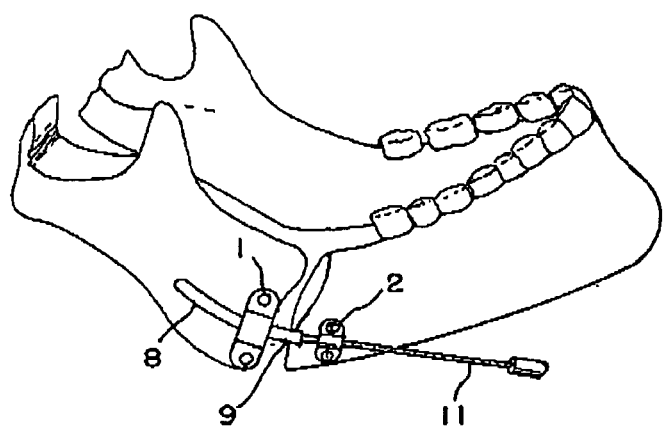
FIG. 2 is a perspective view showing the distractor after distraction has occurred.
Figure 3:
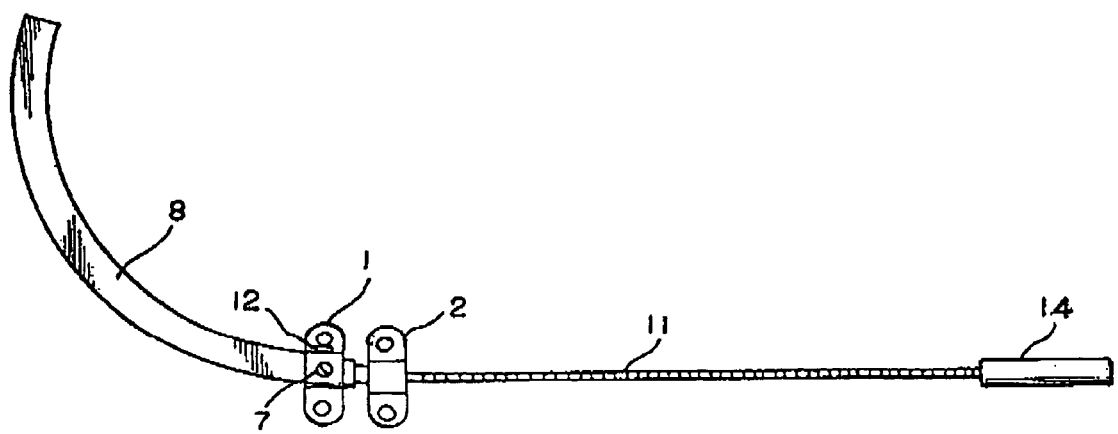
FIG. 3 is an enlarged side view of the distractor.
Figure 4:
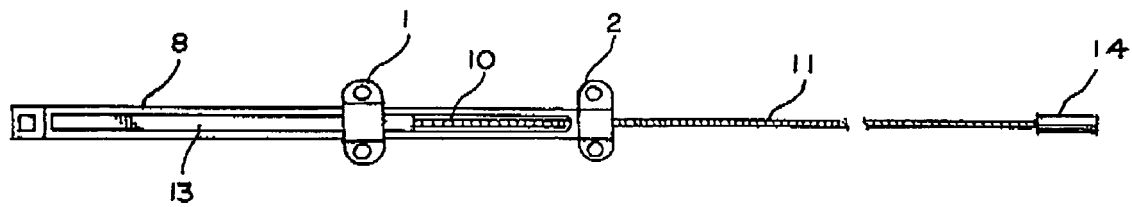
FIG. 4 is a view showing the internal groove of the distractor.

Then, in order to initiate distraction, nut 14 is rotated to cause drive screw 11 to rotate through the internal threads of mount 2 and into an abutting relationship with stop screw 12 thereby causing mount 2 to move away from mount 1 and telescoping extension 9 to withdraw from curved channel 8 into positions, as shown in FIG. 2, whereby distraction is complete and osteogenesis is initiated.

Therefore, by this invention, since curved channel 8 is shaped in the form of a logarithmic curve, the number of distractor channels necessary to complete a distraction is greatly reduced. Channels shaped of circle segment require up to six channels to accomplish the same task that two channels in the form of a logarithmic curve require.

Also, in known distractors, an open slot is formed on the outer surface of the curved channel and, if the drive screw breaks, it will extend out of the channel thereby rendering the distractor ineffective. According to this invention, since there is no open slot on the outer surface of the curved channel, if the drive screw should break, treatment continues without interruption.

Another advantage is the universal nature of the distractor and the telescoping extension such that the distractor can be placed on either side of a patient's mouth. Known distractors require separate right and left handed devices.

The invention claimed is:

1. An orthodontic distractor comprising a pair of mounts, a curved channel disposed within one of said mounts, a hollow extension telescopically disposed within said curved channel, a drive screw having an inner end threadedly interconnected with the other of said mounts, means to prevent movement of said drive screw within said channel comprising a stop screw threaded into said one mount, a groove formed on the inner surface of said curved channel, and said stop screw disposed in said groove with said inner end of said drive screw in abutting engagement with said stop screw.

2. An orthodontic distractor according to claim 1 wherein said channel is in the form of a logarithmic curve.

3. An orthodontic distractor according to claim 1 wherein said mounts are attachable to bone by means of screws.

4. An orthodontic distractor according to claim 1 wherein a nut is formed on the free end of said drive screw.

* * * * *